United States Patent
Ralph et al.

(10) Patent No.: US 8,048,159 B2
(45) Date of Patent: *Nov. 1, 2011

(54) ARTIFICIAL INTERVERTEBRAL DISC HAVING A SLOTTED BELLEVILLE WASHER FORCE RESTORING ELEMENT

(75) Inventors: James D. Ralph, Seaside Park, NJ (US); Stephen Tatar, Montville, NJ (US)

(73) Assignee: SpineCore, Inc., Allendale, NJ (US)

( * ) Notice: Subject to any disclaimer, the term of this patent is extended or adjusted under 35 U.S.C. 154(b) by 1386 days.

This patent is subject to a terminal disclaimer.

(21) Appl. No.: 11/157,551

(22) Filed: Jun. 21, 2005

(65) Prior Publication Data
US 2005/0234554 A1 Oct. 20, 2005

Related U.S. Application Data

(63) Continuation of application No. 10/177,013, filed on Jun. 21, 2002, now Pat. No. 6,918,934, which is a continuation-in-part of application No. 09/968,045, filed on Oct. 1, 2001, now Pat. No. 6,740,117.

(51) Int. Cl.
*A61F 2/44* (2006.01)
(52) U.S. Cl. .................................. 623/17.14; 623/17.15
(58) Field of Classification Search ................ 623/17.13, 623/17.14, 17.15
See application file for complete search history.

(56) References Cited

U.S. PATENT DOCUMENTS

| 1,641,059 | A |   | 8/1927  | Tausch |
|-----------|---|---|---------|--------|
| 4,024,829 | A | * | 5/1977  | Su ............................... 116/34 R |
| 4,303,001 | A |   | 12/1981 | Trungold |
| 4,318,627 | A |   | 3/1982  | Morin et al. |
| 4,481,655 | A |   | 11/1984 | Annis et al. |
| 4,759,769 | A |   | 7/1988  | Hedman et al. |
| 4,932,969 | A |   | 6/1990  | Frey et al. |
| 4,958,970 | A |   | 9/1990  | Rose et al. |
| 5,034,254 | A |   | 7/1991  | Cologna et al. |
| 5,370,697 | A |   | 12/1994 | Baumgartner |

(Continued)

FOREIGN PATENT DOCUMENTS

DE 2263842 A1 7/1974

(Continued)

OTHER PUBLICATIONS

European Search Report, EP 10152823, dated Mar. 22, 2010.

*Primary Examiner* — Brian E. Pellegrino
(74) *Attorney, Agent, or Firm* — Lerner, David, Littenberg, Krumholz & Mentlik, LLP

(57) ABSTRACT

An intervertebral spacer device includes first and second plates disposed in a spaced apart relationship, each plate having an inner surface and an outer surface, the inner surfaces of the opposing plates facing one another. The device also includes a restoring force providing element disposed between the inner surfaces of the plates. The restoring force providing element includes a slotted belleville washer having a convex shape when unloaded and a flatter shape when loaded, whereby one or more slots of the belleville washer widen when compressively loaded. The second plate has an annular groove formed in the inner surface of the second plate, the device including a retaining wall and a retaining ring, whereby a wide end of the belleville washer is captured by the retaining wall and the retaining ring for maintaining the wide end adjacent the inner surface of the second plate.

14 Claims, 11 Drawing Sheets

U.S. PATENT DOCUMENTS

| | | |
|---|---|---|
| 5,458,642 A | 10/1995 | Beer et al. |
| 5,535,861 A | 7/1996 | Young |
| 5,556,431 A | 9/1996 | Buttner-Janz |
| 5,562,738 A | 10/1996 | Boyd et al. |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,755,796 A | 5/1998 | Ibo et al. |
| 5,827,328 A | 10/1998 | Buttermann |
| 5,865,846 A | 2/1999 | Bryan et al. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,989,291 A | 11/1999 | Ralph et al. |
| 6,001,130 A | 12/1999 | Bryan et al. |
| 6,019,792 A | 2/2000 | Cauthen |
| 6,039,763 A | 3/2000 | Shelokov |
| 6,063,121 A | 5/2000 | Xavier et al. |
| 6,113,637 A | 9/2000 | Gill et al. |
| 6,136,031 A | 10/2000 | Middleton |
| 6,146,421 A | 11/2000 | Gordon et al. |
| 6,156,067 A | 12/2000 | Bryan et al. |
| 6,179,874 B1 | 1/2001 | Cauthen |
| 6,228,118 B1 | 5/2001 | Gordon |
| 6,368,350 B1 | 4/2002 | Erickson et al. |
| 6,468,310 B1 | 10/2002 | Ralph et al. |
| 6,485,491 B1 | 11/2002 | Farris et al. |
| 6,488,710 B2 | 12/2002 | Besselink et al. |
| 6,740,117 B2 * | 5/2004 | Ralph et al. ............... 623/17.14 |
| 6,863,689 B2 | 3/2005 | Ralph et al. |
| 6,918,934 B2 * | 7/2005 | Ralph et al. ............... 623/17.14 |
| 7,048,763 B2 | 5/2006 | Ralph et al. |
| 7,208,014 B2 | 4/2007 | Ralph et al. |
| 2002/0035400 A1 | 3/2002 | Bryan et al. |
| 2003/0069642 A1 | 4/2003 | Ralph et al. |
| 2005/0234554 A1 | 10/2005 | Ralph et al. |

FOREIGN PATENT DOCUMENTS

| | | |
|---|---|---|
| EP | 0566810 A1 | 10/1993 |
| FR | 2775587 A1 | 9/1999 |
| WO | 03007779 A2 | 1/2003 |

* cited by examiner

ARTIFICIAL INTERVERTEBRAL DISC HAVING A SLOTTED BELLEVILLE WASHER FORCE RESTORING ELEMENT

CROSS-REFERENCE TO RELATED APPLICATIONS

This application is a continuation of U.S. patent application Ser. No. 10/177,013, filed Jun. 21, 2002, now U.S. Pat. No. 6,918,934, which is a continuation-in-part of U.S. patent application Ser. No. 09/968,045, entitled "Intervertebral Spacer Device Having a Radially Thinning Slotted Belleville Spring," filed Oct. 1, 2001, now U.S. Pat. No. 6,740,117, the disclosures of which are hereby incorporated by reference herein.

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device that utilizes a slotted belleville washer as a restoring force providing element.

BACKGROUND OF THE INVENTION

The bones and connective tissue of an adult human spinal column consists of more than 20 discrete bones coupled sequentially to one another by a tri-joint complex that consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine includes the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than 20 bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determines the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional materials, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the invention to provide an intervertebral spacer that stabilizes the spine without promoting a bone fusion across the intervertebral space.

It is further an object of the invention to provide an implant device that stabilizes the spine while still permitting normal motion.

It is further an object of the invention to provide a device for implantation into the intervertebral space that does not promote the abnormal distribution of biomechanical stresses on the patient's spine.

It is further an object of the invention to provide an artificial disc that has an plate attachment device (for attaching the plates of the artificial disc to the vertebral bones between which the disc is implanted) with superior gripping and holding strength upon initial implantation and thereafter.

It is further an object of the invention to provide an artificial disc plate attachment device that deflects during insertion of the artificial disc between vertebral bodies.

It is further an object of the invention to provide an artificial disc plate attachment device that conforms to the concave surface of a vertebral body.

It is further an object of the invention to provide an artificial disc plate attachment device that does not restrict the angle at which the artificial disc can be implanted.

It is further an object of the invention to provide an artificial disc that supports tension loads.

It is further an object of the invention to provide an artificial disc that provides a centroid of motion centrally located within the intervertebral space.

Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which is an artificial intervertebral disc or intervertebral spacer device comprising a pair of support members (e.g., spaced apart plates), each with an exterior surface. Because the artificial disc is to be positioned between the facing surfaces of adjacent vertebral bodies, the plates are arranged in a substantially parallel planar alignment (or slightly offset relative to one another in accordance with proper lordotic angulation) with the exterior surfaces facing away from one another. The plates are to mate with the vertebral bodies so as to not rotate relative thereto, but rather to permit the spinal segments to axially compress and bend relative to one another in manners that mimic the natural motion of the spinal segment. This natural motion is permitted by the performance of a spring disposed between the secured plates, and the securing of the plates to the vertebral bone is preferably achieved through the use of a vertebral body contact element including, for example, a convex mesh attached to the exterior surface of each plate. Each convex mesh is secured at its perimeter, by laser welds, to the exterior surface of the respective plate. While domed in its initial undeflected conformation, the mesh deflects as necessary during insertion of the artificial disc between vertebral bodies, and, once the artificial disc is seated between the vertebral bodies, the mesh deforms as necessary under anatomical loads to reshape itself to the concave surface of the vertebral endplate. Thus, the wire mesh is deformably reshapeable under anatomical loads such that it conformably deflects against the concave surface to securably engage the vertebral body endplate. Stated alternatively, because the wire mesh is convexly shaped and is secured at its perimeter to the plate, the wire mesh is biased away from the plate but moveable toward the plate (under a load overcoming the bias; such a load is present, for example, as an anatomical load in the intervertebral space) so that it will securably engage the vertebral body endplate when disposed in the intervertebral space. This affords the plate having the mesh substantially superior gripping and holding strength upon initial implantation, as compared with other artificial disc products. The convex mesh further provides an osteoconductive surface through which the bone may ultimately grow. The mesh preferably is comprised of titanium, but can also be formed from other metals and/or non-metals. Inasmuch as the mesh is domed, it does not restrict the angle at which the artificial disc can be implanted. It should be understood that while the flexible dome is described herein preferably as a wire mesh, other meshed or solid flexible elements can also be used, including flexible elements comprises of non-metals and/or other metals. Further, the flexibility, deflectability and/or deformability need not be provided by a flexible material, but can additionally or alternatively be provided mechanically or by other means.

To enhance the securing of the plates to the vertebral bones, plates in some embodiments further comprise at least a lateral porous ring (which may be, for example, a sprayed deposition layer, or an adhesive applied beaded metal layer, or another suitable porous coating known in the art). This porous ring permits the long-term ingrowth of vertebral bone into the plate, thus permanently securing the prosthesis within the intervertebral space. The porous layer may extend beneath the domed mesh as well, but is more importantly applied to the lateral rim of the exterior surface of the plate that seats directly against the vertebral body.

Between the plates, on the exterior of the device, there may also be included a circumferential wall that is resilient and that prevents vessels and tissues from entering the interior of the device. This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials, which could be utilized herein, may be found in the field of orthopedic in conjunction with ligament and tendon repair. It is anticipated that future developments in this area will produce materials, which are compatible for use with this invention, the breadth of which shall not be limited by the choice of such a material. For the purposes of this description, however, it shall be understood that such a circumferential wall is unnecessary, and in some instances may be a hindrance, and thusly is not included in the specific embodiments set forth hereinbelow.

The spring disposed between the plates provides a strong restoring force when a compressive load is applied to the plates, and also permits rotation and angulation of the two plates relative to one another. While there is a wide variety of artificial disc embodiments contemplated, four embodiment families are described herein, each including at least one slotted belleville washer, as representative of preferred types.

Belleville washers are washers that are generally bowed in the radial direction. Specifically, they have a radial convexity (i.e., the height of the washer is not linearly related to the radial distance, but may, for example, be parabolic in shape). The restoring force of a belleville washer is proportional to the elastic properties of the material. As a compressive load is applied to a belleville washer, the forces are directed into a hoop stress that tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force that is proportional to the elastic modulus of the material in a hoop stressed condition. In general, a belleville washer is one of the strongest configurations for a spring, and is highly suitable for use as a restoring force providing subassembly in an intervertebral spacer element that must endure considerable cyclical loading in an active human adult.

In a first embodiment family of the invention, two belleville washers are oriented such that the two raised conical ends of the washers are facing one another. The wider ends of the washers (at least one of which is slotted) are compressed and/or coupled to the respective inner surfaces of the plates. A compressive load applied to the plates causes the corresponding compression of the belleville washers, which in turn causes a restoring force to be applied to the plates. The magnitudes of the compressive load support and the restoring force provided by the belleville washer are modified (relative to those of an unslotted belleville washer) by the slots that are provided in the washer. As noted above, at least one of the belleville washers is slotted, preferably with spiral slots initiating on the periphery of the washer and extending along arcs that are generally radially inwardly directed a distance toward the center of the bowed disc. The slots of the belleville washer allow the washer expand radially as the slots widen under the load, only to spring back into its undeflected shape upon the unloading of the spring. With slots formed in the washer, it expands and restores itself far more elastically than a solid washer. It shall be understood that the belleville washers may rotate and angulate relative to one another without interfering with the restoring force they provide to the plates. In this way the plates may rotate and angulate relative to one another while maintaining a constant resilient capacity relative to the adjacent bone.

In a second embodiment family of the invention, a single modified and spirally slotted belleville washer is utilized in conjunction with a semispherical protuberance (e.g., a ball-shaped headed post) on which it is free to rotate and angulate through a range of angles (thus permitting the plates to rotate and angulate relative to one another through a corresponding range of angles). More particularly, embodiments in this second embodiment family comprise a pair of spaced apart plates, one of which is simply a disc shaped member having external and internal flat faces (outer and inner flat surfaces). The other of the plates is similarly shaped, having a flat exterior surface, but further including a short central post portion that rises out of the interior face at a nearly perpendicular angle. The top of this short post portion includes a ball-shaped knob. The knob includes a central axial bore that receives a deflection preventing element (e.g., a rivet, set screw, plug, or dowel; a set screw is used herein as an example, the bore is correspondingly threaded to accept it). Prior to the insertion of the set screw, the ball-shaped head can deflect radially inward (so that the ball-shaped knob contracts). The insertion of the set screw eliminates the capacity for this deflection.

The spirally slotted belleville washer is mounted to this ball-shaped knob in such a way that it may rotate and angulate freely through a range of angles equivalent to the fraction of normal human spine rotation (to mimic normal disc rotation). The belleville washer is modified by including a curvate socket (e.g., provided by an enlarged inner circumferential portion at the center of the washer) that accommodates the ball-shaped portion of the post. More particularly, the enlarged portion includes a curvate volume having a substantially constant radius of curvature that is also substantially equivalent to the radius of the ball-shaped head of the post. The deflectability of the ball-shaped head of the post, prior to the insertion of the set screw, permits the head to be inserted into the interior volume at the center of the belleville washer. Subsequent introduction of the set screw into the axial bore of the post prevents the head from deflecting again, securing the head in the curvate socket, such that the head can rotate and angulate therein, but not escape therefrom. Thereby, the washer can be secured to the ball-shaped head so that it can rotate and angulate thereon through a range of proper lordotic angles (in some embodiments, a tightening of the set screw locks the washer on the ball-shaped head at one of the lordotic angles). This assembly provides ample spring-like performance with respect to axial compressive loads, as well as long cycle life to mimic the axial biomechanical performance of the normal human intervertebral disc.

In a third embodiment family of the invention, the spirally slotted belleville washers utilized have a radially varying thickness. Some belleville washers comprise a radially varying thickness that grows thicker as the radius increases (the thickness is directly proportional to the radius). Other belleville washers comprise a radially varying thickness that grows thinner as the radius increases (the thickness is inversely proportional to the radius). Either way, superior reproduction of the anatomical deflection to load characteristics is achieved. The purpose is to create a non-linear load deflection profile by permitting a portion of the washer to deflect early in the loading, and a more rigid portion to deflect only under more severe loadings. By varying the thickness of the washer material smoothly across its radial extent, this goal is achieved.

Preferably, in the third embodiment family, the spirally slotted belleville washer is utilized in conjunction with a semispherical protuberance (e.g., a ball-shaped headed post) on which it is free to rotate and angulate through a range of angles, similar in this respect to the embodiments in the second embodiment family. The upper plate in these embodiments is different than that of the upper plate in the embodiments in the second embodiment family in that it includes a circular retaining wall and a retaining ring for housing therein the wide end of the selected belleville washer. As the washer compresses and decompresses, the annular retaining wall maintains the wide end of the washer within a prescribed boundary on the internal face of the plate which it contacts, and an annular retaining ring maintains the wide end of the washer against the internal face. Further, the belleville washer is modified by including a curvate socket (e.g., an enlarged portion with a curvate volume) that accommodates the ball-shaped portion of the post, similar in this respect to the washers in the second embodiment family. It should be understood that the lower plate of the type used in the third embodiment family can be used in the first and second embodiment families, and vice versa, without departing from the scope of the invention.

Embodiments of the fourth embodiment family preferably comprise alternate plates, preferably in conjunction with a shield member, to achieve the same functionality as the plates of the first, second and third embodiment families, and are for use with any of the belleville washers described herein. More particularly, a lower plate of the fourth embodiment family has a circular recess in the inner face (inwardly facing surface) of the plate, which circular recess has a circumferential wall having the purpose and functionality of the annular retaining wall described above. The lower plate also utilizes a shield member placed over the belleville washer (when the belleville washer is disposed in the circular recess) and secured to the plate at the perimeter of the shield, which shield member has the purpose and functionality of the annular retaining ring described above. Preferably, the shield member is frusto-conical in shape so that it has a central hole to permit passage therethrough of the ball-shaped head and post of the opposing plate during assembly. An opposing plate, having a semispherical protuberance with radial slots and an axial bore (for receiving a deflection preventing element such as, for example, a rivet), provides functionality similar to the ball-shaped headed post described above, but with a lower profile. Both of the plates preferably have the convex mesh described above for securing to adjacent vertebral bones.

With the several types of plates, the several types of belleville washers, and the several manners in which they may be coupled together, it is possible to assemble a variety of artificial disc embodiments. Many examples are described herein as noted above, although many permutations that are contemplated and encompassed by the invention are not specifically identified herein, but are readily identifiable with an understanding of the invention as described.

Each assembly enjoys spring-like performance with respect to axial compressive loads, as well as long cycle life to mimic the axial biomechanical performance of the normal human intervertebral disc. The slots of the belleville washers allow the washers to expand radially as the slots widen under the load, only to spring back into an undeflected shape upon the unloading of the spring. As each washer compresses and decompresses, the annual retaining wall (or circular recess wall) maintains the wide end of the washer within a prescribed boundary on the internal face of the plate that it contacts. Further, the assemblies withstand tension loads on the outwardly facing surfaces, because the annular retaining ring (or retaining shield) maintains the wide end of the washer against the internal face, and the set screw (or rivet) in the axial bore prevents the semispherical protuberance (either variation) from deflecting, thus preventing it from exiting the curvate socket. Accordingly, once the plates are secured to the vertebral bones, the assembly will not come apart when a normally experienced tension load is applied to the spine, similar to the tension-bearing integrity of a healthy natural intervertebral disc.

Assemblies having the ball-and-socket joint also provide a centroid of motion centrally located within the intervertebral space, because the plates are made rotatable and angulatable relative to one another by the semispherical protuberance being rotatably and angulatably coupled in the curvate socket. The centroid of motion remains in the semispherical protuberance, and thus remains centrally located between the vertebral bodies, similar to the centroid of motion in a healthy natural intervertebral disc. Finally, inasmuch as the human body has a tendency to produce fibrous tissues in perceived voids, such as may be found within the interior of the invention, and such fibrous tissues may interfere with the stable and/or predicted functioning of the device, some embodiments of the invention (although not in preferred embodiments) will be filled with a highly resilient elastomeric material. The material itself should be highly biologically inert, and should not substantially interfere with the restoring forces provided by the spring-like mechanisms therein. Suitable materials may include hydrophilic monomers such as are used in contact lenses. Alternative materials include silicone jellies and collagens such as have been used in cosmetic applications. As with the exterior circumferential wall, which was described above as having a variety of suitable alternative materials, it is anticipated that future research will produce alternatives to the materials described herein, and that the future existence of such materials which may be used in conjunction with the invention shall not limit the breadth thereof.

BRIEF DESCRIPTION OF THE DRAWINGS

FIG. 12a is a top view of the plate having the circumferential skirt and retaining ring, in which a belleville washer of the type of either FIG. 11a or 11b is disposed within the skirt, and FIG. 12b is a top view of the plate having a post element that seats within the central opening of the belleville washer.

DETAILED DESCRIPTION OF THE PREFERRED EMBODIMENT

Figure 1:
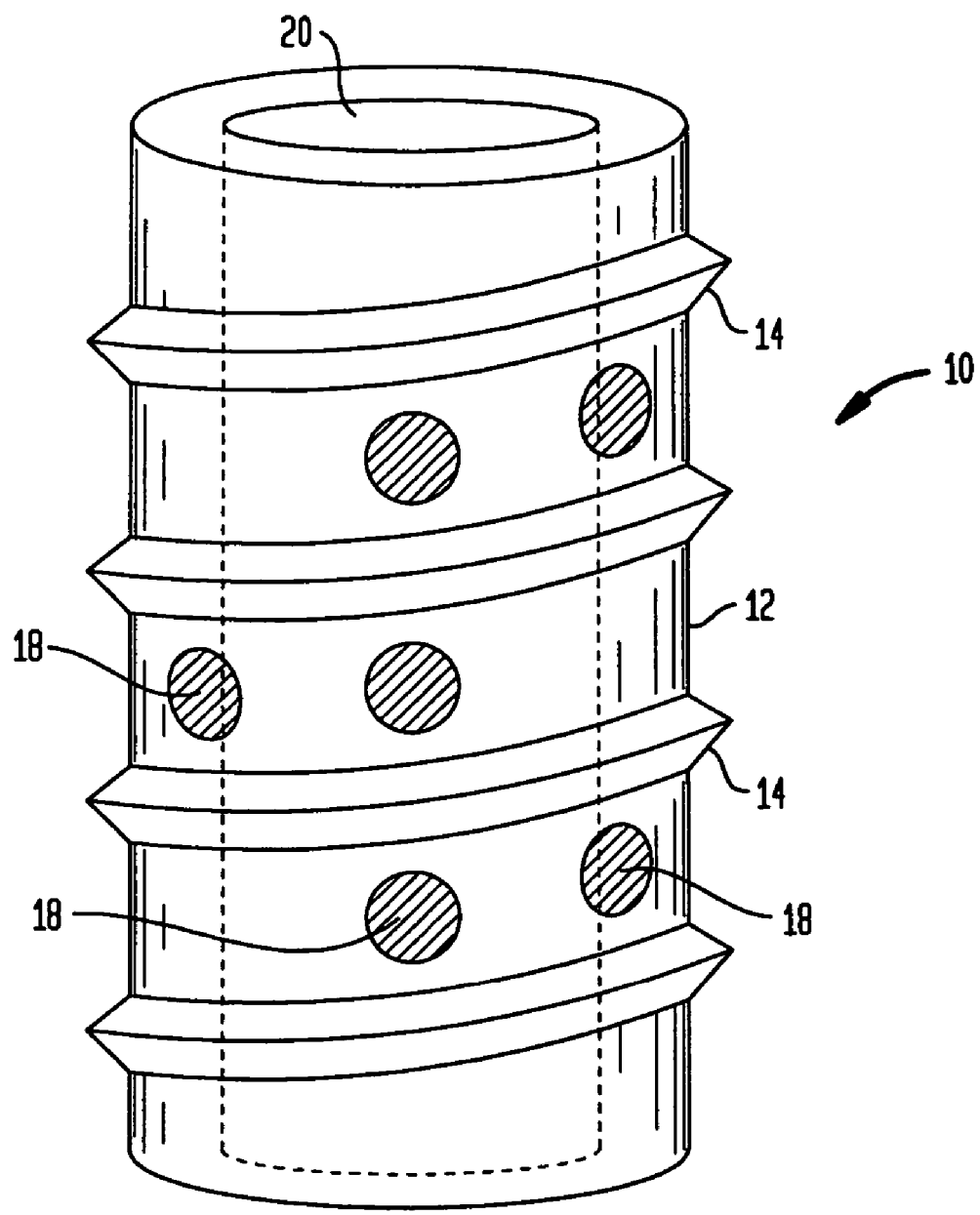
FIG. 1 is a side perspective view of an interbody fusion device of the prior art.
Figure 2:
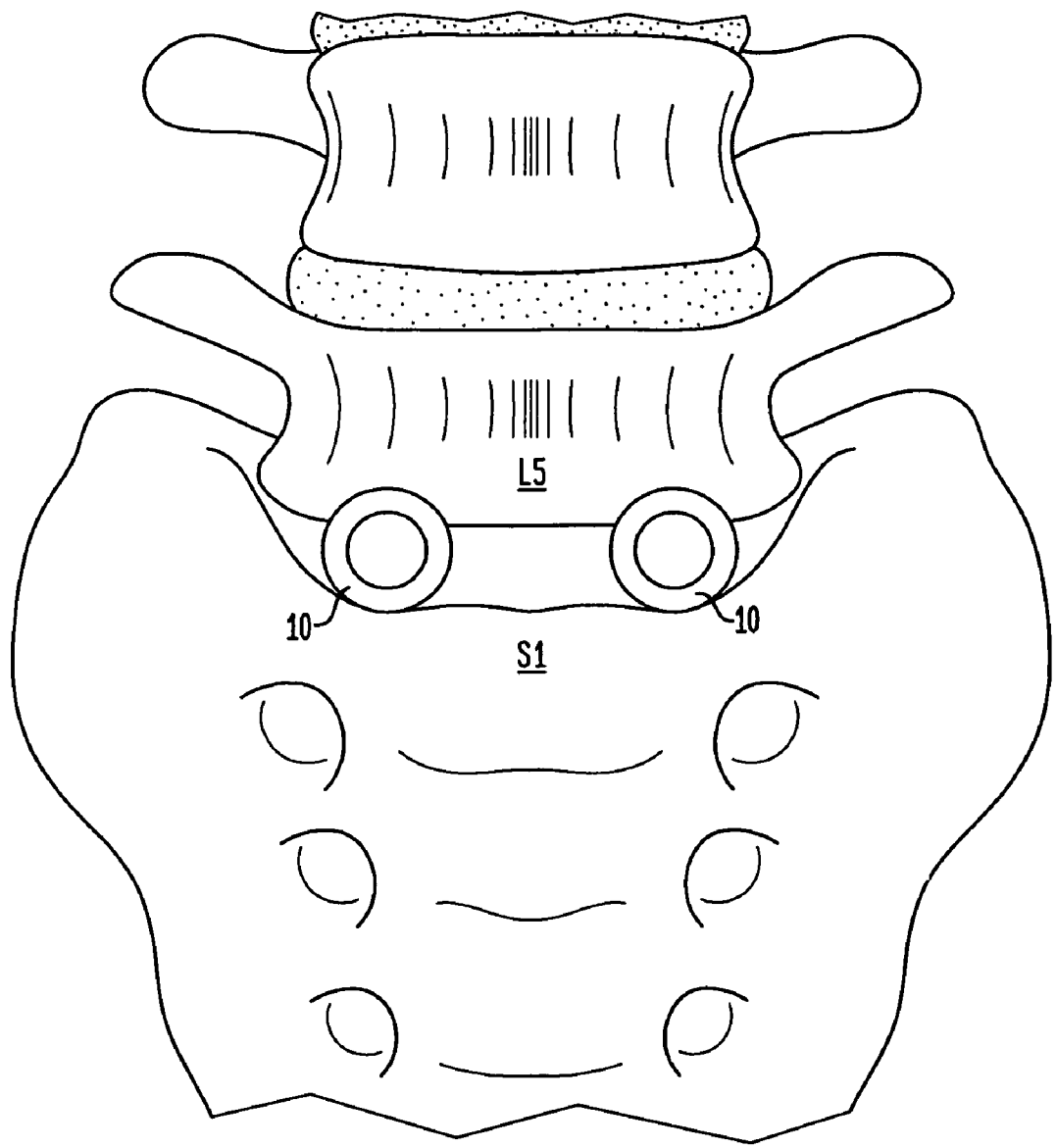
FIG. 2 is a front view of the anterior portion of the lumbosacral region of a human spine, into which a pair of interbody fusion devices of the type shown in FIG. 1 have been implanted.

While the invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the invention and not as limiting of such broad scope. Like numbers refer to similar features of like elements throughout. With regard to the first embodiment family, and referring now to FIGS. 3a-b, side cross-section views of the upper and lower plates 100a,100b of a first embodiment family of the invention are shown. (As with all embodiments described herein, "upper" and "lower" are merely visual designations to describe the positions of the plates in accordance with the illustrations; it should be understood that the invention encompasses embodiments where the "upper" plates serve as lower plates and "lower" plates serve as upper plates.) More particularly, the upper and lower plates 100a,100b are identical. As the device is designed to be positioned between the facing surfaces of adjacent vertebral bodies, the plates include substantially flat surface portions 102a,102b that seat against the opposing bone surfaces. In addition, the plates are to mate with the bone surfaces in such a way as to not rotate relative thereto. Therefore, the plates include a porous coating 104a,104b into which the bone of the vertebral body can grow. (Note that this limited fusion of the bone to the plate does not extend across the intervertebral space.) An additional hole 106a,106b is provided in each plate such that the interior of the device may be readily accessed if necessary.

The plates 100a, 100b further include a circumferential skirt comprised of an offset flange 108a,108b. The offset corresponds to the front 110a, 110b and rear 111a, 111b orientation of the overall assembly. More particularly, the offset nature of the flanges 108a,108b is exhibited in the non-symmetric appearance of each flange as it circumscribes the corresponding plate 100a, 100b. By this it is meant that the portion of the flange 108a,108b that corresponds to the rear 111a, 111b of the device is shorter than the portion corresponding to the front 110a, 110b of the device.

Figure 3A:
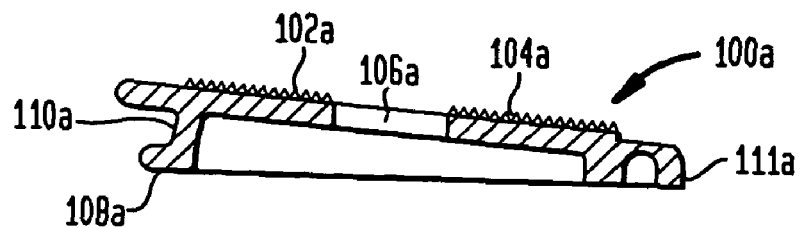
FIGS. 3a-b are side cross-section views of upper and lower opposing plates of a first embodiment family of the invention.
Figure 3B:
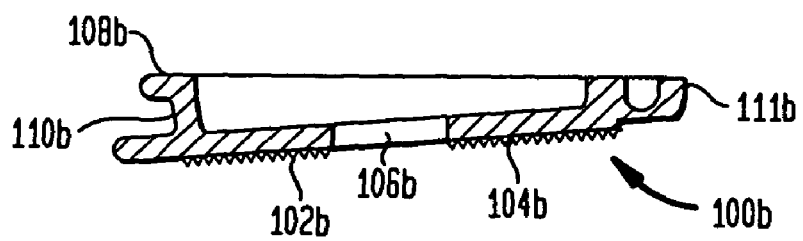
Figure 4:
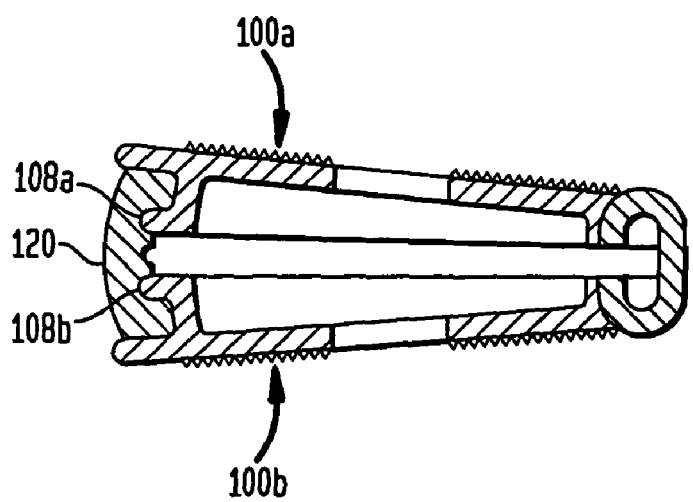
FIG. 4 is a side cross-section view of the opposing plates of the first embodiment family in association with one another.

Referring now to FIG. 4, an embodiment in the first embodiment family is shown partially assembled in a side cross-section view, wherein the upper and lower plates 100a, 100b illustrated in FIGS. 3a-b are joined by means of a circumferential wall 120. More particularly, between the plates 100a, 100b, on the exterior of the device, there is included a circumferential wall 120 that is resilient and that is provided to prevent vessels and tissues from entering within the interior of the device. It is preferred that the resilient wall 120 comprise a porous fabric or a semi-impermeable elastomeric material. The wall 120 is further designed to couple to the flanges 108a, 108b of the corresponding plates 100a, 100b.

Figure 5A:
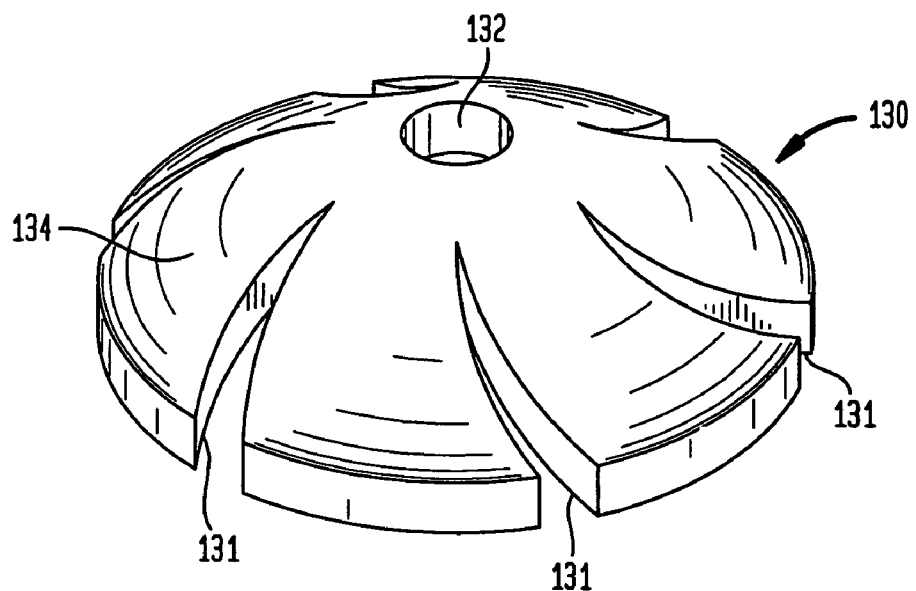
FIGS. 5a-b are perspective and top views of a spirally slotted belleville washer of the first embodiment family.
Figure 5B:
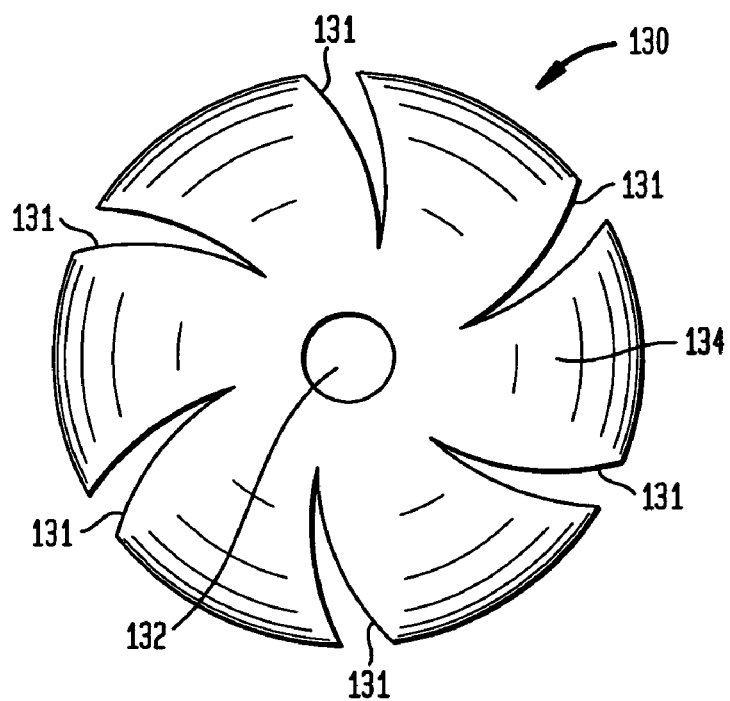

Referring now to FIGS. 5a-b, a belleville washer 130 is provided in a perspective view and a top view, respectively. A belleville washer 130 is a restoring force providing device that comprises a circular shape, having a central opening 132, and which is radially arched in shape (it should be understood that belleville washers having a straight radial extent, e.g., such that they are frusto-conical, can also be used). Most belleville washers have a radial convexity 134 (i.e., the height of the washer 130 is not linearly related to the radial distance, but may, for example, be , parabolic in shape). The restoring force of a belleville washer is proportional to the elastic properties of the material.

The belleville washer 130 further comprises a series of slots 131 formed therein (preferably, but not necessarily, spiral slots as shown). The slots 131 extend from the outer diameter of the belleville washer, inward along arcs generally directed toward the center of the element. The slots 131 do not extend fully to the center of the device. Preferably, the slots extend anywhere from a quarter to three quarters of the overall radius of the washer, depending upon the requirements of the patient, and the anatomical requirements of the device.

As a compressive load is applied to a belleville washer, the forces are directed into a hoop stress that tends to radially expand the washer. This hoop stress is counterbalanced by the material strength of the washer, and the force necessary to widen the spiral slots along with the strain of the material causes a deflection in the height of the washer. Stated equivalently, a belleville washer responds to a compressive load by deflecting compressively; the spirally slotted washer further responds to the load by spreading as the slots in the washer expand under the load. The spring, therefore, provides a restoring force that is proportional to the elastic modulus of the material in both a hoop stressed condition.

Figure 6:
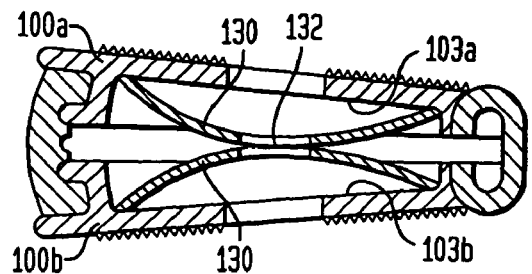
FIG. 6 is a side cross-section fully assembled embodiment in the first embodiment family, which utilizes a pair of spirally slotted belleville washers, both of which are the type shown in FIGS. 5a-b.

Referring now to FIG. 6, the embodiment of FIG. 4 is shown fully assembled in a side cross-section view. The embodiment comprises two belleville washers 130 (at least one of which is spirally slotted) that are oriented such that the two central openings 132 of the raised conical ends of the washers 130 are facing one another. The wider ends of the washers 130 are compressibly retained in the interior of the device, between the inner surfaces 103a, 103b of the plates 100a, 100b. As a result, a compressive load applied to the plates 100a, 100b causes the corresponding compression of the belleville washers 130, which in turn causes a restoring force to be applied to the plates 100a, 100b.

Figure 7:
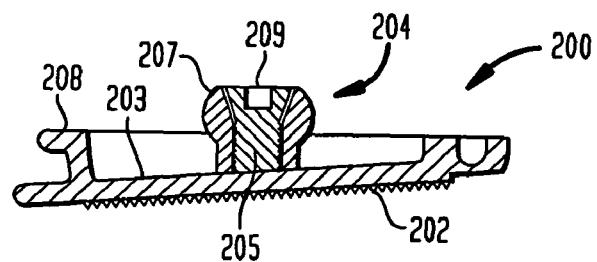
FIG. 7 is a side cross-section view of a lower opposing plate of a second embodiment family of the invention.

With regard to the second embodiment family, and referring now to FIG. 7, a lower plate 200 of a second embodiment family is shown in a side cross-section view. The plate 200 is similarly shaped to the plates described above in the first embodiment family (i.e., having a flat exterior surface 202 and a circumferential flange 208), but further includes a semispherical protuberance (e.g., a short central post member 204 having a ball-shaped head 207) that rises out of the interior face 203 at a nearly perpendicular angle. The top of this short post member 204 includes the ball-shaped head 207. The head 207 includes a central axial bore 209 that extends down the post 204. This bore 209 is designed to receive a deflection preventing element (e.g., a rivet, plug, dowel, or set screw; a set screw 205 is used herein as an example, and the bore is correspondingly threaded to accept it). Prior to the insertion of the set screw 205, the ball-shaped head 207 of the post 204 can deflect radially inward (so that the ball-shaped head contracts). The insertion of the set screw 205 eliminates the capacity for this deflection.

Figure 8:
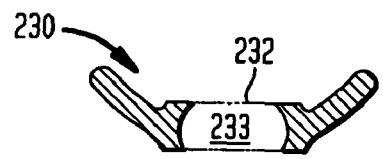
FIG. 8 is a side cross-section view of a modified spirally slotted belleville washer of the second embodiment family.

Referring now to FIG. 8, a modified and spirally slotted belleville washer 230 of the second embodiment family is shown in a side cross-section view. This belleville washer design is similar to the belleville washer design described above with respect to FIGS. 5a-b, but with an additional feature of having a curvate socket (e.g., an enlarged central opening 232 having a curvate volume 233) for receiving therein the ball-shaped head 207 of the post 204 of the lower plate 200 described above. More particularly, the curvate volume 233 has a substantially constant radius of curvature that is also substantially equivalent to the radius of the ball-shaped head 207 of the post 204. The spiral slots should not extend all the way to the central opening, and should approach the opening only as far as the material strength of the washer can handle without plastically deforming under the expected anatomical loading.

Figure 9:
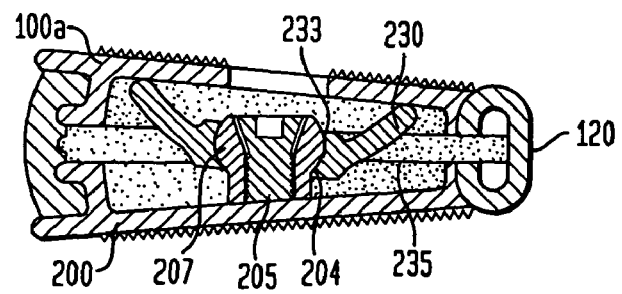
FIG. 9 is a side cross-section fully assembled embodiment in the second embodiment family, which utilizes a single modified spirally slotted belleville washer of the type shown in FIG. 8.

Referring also to FIG. 9, in which an embodiment of the second embodiment family is shown fully assembled, the deflectability of the ball-shaped head 207 of the post 204, prior to the insertion of the set screw 205, permits the head 207 to be inserted into the interior volume 233 at the center of the modified belleville washer 230. Subsequent introduction of the set screw 205 into the axial bore 209 of the post 204 prevents the head 207 from escaping the belleville washer 230, providing the ability for the device to handle tension loading. Thereby, the head 207 is secured in the socket 233 so that it can rotate and angulate freely therein.

Figure 10A:
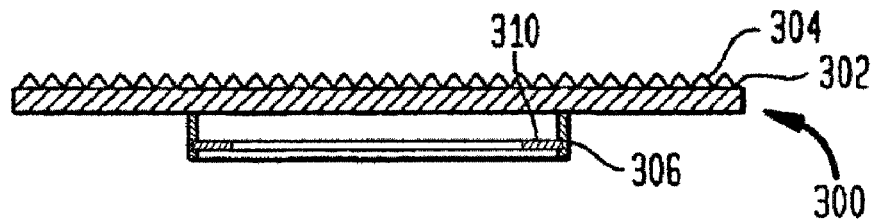
FIGS. 10a-b are side cross-section views of upper and lower opposing plates of a third embodiment family of the invention.
Figure 10B:
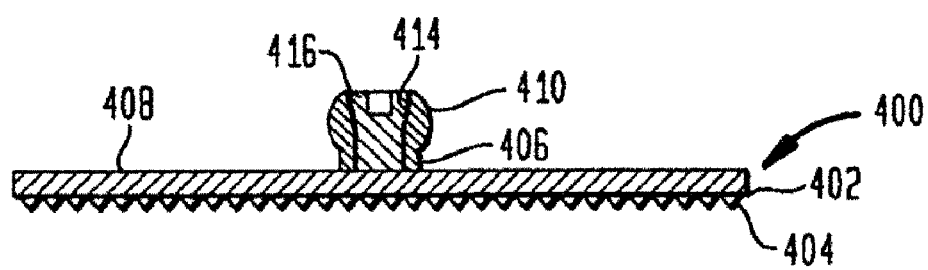
Figure 10C:
FIGS. 10c-d show respective cross-sectional views of upper and lower plates, in accordance with another preferred embodiment of the present invention.
Figure 10D:
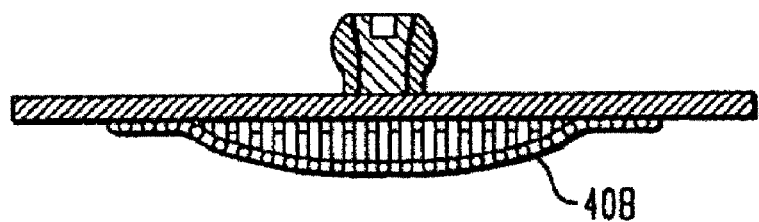

With regard to the third embodiment family, and referring now to FIGS. 10a-b, side cross-section views of the upper and lower plates 300, 400 of a third embodiment family are shown. Similar to the plates 100a, 200 of the second embodiment, the plates 300, 400 have substantially flat surface portions 302, 402 that seat against the opposing bone surfaces and a porous coating 304, 404 into which the bone of the vertebral body can grow. As shown in FIGS. 10c-d, the most desirable upper and lower plate surface porous feature is a deflectable mesh 408 (preferable of metal) into which the bone can readily grow, and which mesh will deform to seat into the concave upper and lower bone faces. (Note that this limited fusion of the bone to the plate does not extend across the intervertebral space.) These features, while being preferred are not required, and further can be used with any of the embodiments described herein, as well as other embodiments and for other intervertebral spacer devices and the like.

Figure 12A:
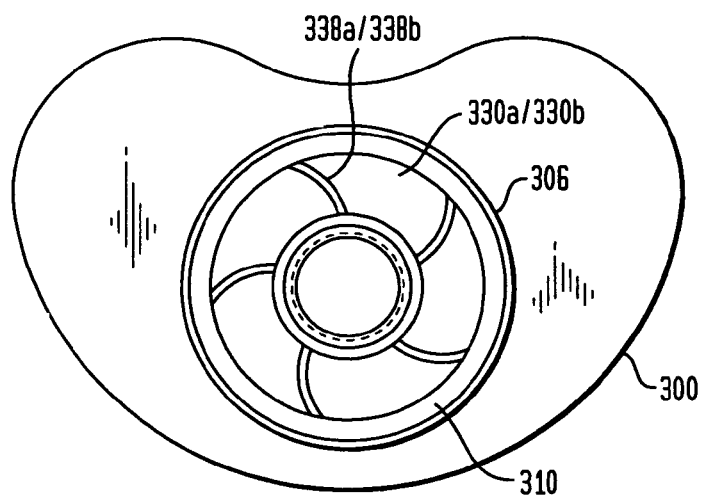
FIGS. 12a-b are top views of the opposing plates of FIGS. 10a-b, and more particularly.

Referring now also to FIG. 12a, plate 300 further includes a circumferential skirt 306 that serves as a retaining wall, into which the wide end of a belleville washer may be seated. The diameter of the retaining wall 306 is preferably slightly wider than the diameter of the undeflected belleville washer such that the loading thereof can result in an unrestrained radial deflection of the washer. The inner surface of the retaining wall 306 includes an annular recess into which a retaining ring 310 may be provided for holding the belleville washer in place (see, e.g., the assembled embodiments of FIGS. 13a-b).

Figure 12B:
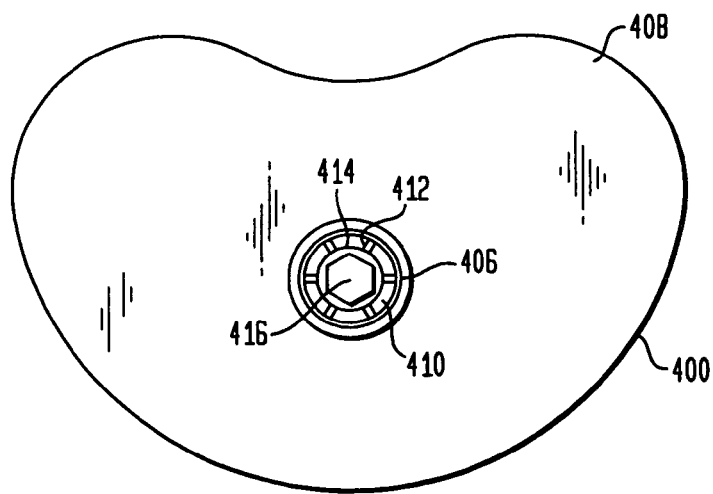

Referring now also to FIG. 12b, plate 400 of the third embodiment family, similar to the plate 200 of the second embodiment family, further includes a semispherical protuberance (e.g., a central post 406 having at its top end a deflectable ball-shaped head 410) with radial slots 412 and an axial bore 414 for receiving a deflection-preventing element (e.g., a rivet, plug, dowel, or set screw; a set screw 416 is used herein as an example) that rises out of the interior face 408 of the plate 400 at a nearly perpendicular angle.

Figure 11A:
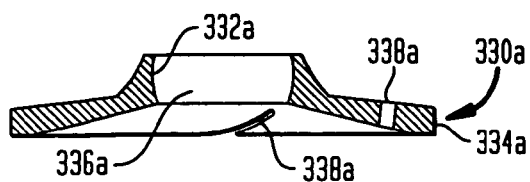
FIGS. 11a-b are cross-section views of belleville washers, having radially varying thicknesses and spiral slots, of the type used in the third embodiment family, the belleville washer of FIG. 11a having a slotted washer shape with a thinner inner portion than outer, the belleville washer of FIG. 11b having a slotted washer shape with a thicker inner portion than outer.
Figure 11B:
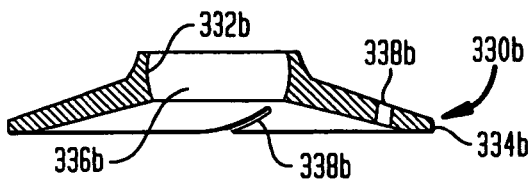

Referring now to FIGS. 11a-b, side cross-section views of two belleville washers 330a, 330b are provided. Each of these belleville washers 330a, 330b is similar in form and function to the belleville washer of the second embodiment family, but with a significant difference in that the thickness (the distance from the concave surface to the convex surface) of the material that comprises the washer varies from the central opening 332a, 332b region to the outer circumference 334a, 334b of the element.

More particularly with respect to the washer in FIG. 11a (and shown within the circumferential ring of plate 300 in FIG. 12a), the belleville washer 330a has a greater thickness at the outer edge 334a than it does at the inner edge 332a. As the restoring force of a belleville washer is proportional to the elastic properties of the material as well as the quantity of material being loaded, the reduction of the material at the edge of the inner opening 332a permits a load/deflection profile in which the load which deflects the inner portion of the washer is less than the outer portion. This permits the washer to compress to initially compress easily under a light loading, but to rapidly (faster than a straight linear loading profile) become stiff and resist deflection. This loading profile is more anatomically relevant with respect to mimicking the performance of the cartilage present in a healthy intervertebral space. The belleville washer 330a further includes a series of spiral slots 338a extending from the outer edge 334a toward the inner opening 332a, similar in form and function to the spiral slots of the belleville washer of the second embodiment family.

More particularly with respect to the washer in FIG. 11b (and shown within the circumferential ring of plate 300 in FIG. 12a), the belleville washer 330b has a smaller thickness at the outer edge 334b than it does at the inner edge 332b. As the restoring force of a belleville washer is proportional to the elastic properties of the material as well as the quantity of material being loaded, the reduction of the material at the outer edge 334b permits a load profile in which the load that deflects the outer portion of the washer is less than the inner portion. This permits the washer to compress to initially compress easily under a light loading (as a result of outer edge deflection), but to rapidly (faster than a straight linear loading profile) become stiff and resist deflection. This loading profile is more anatomically relevant with respect to mimicking the performance of the cartilage present in a healthy intervertebral space. The belleville washer 330b further includes a series of spiral slots 338b extending from the outer edge 334b toward the inner opening 332b, similar in form and function to the spiral slots of the belleville washer of the second embodiment.

Each belleville washer 330a, 330b has a curvate socket for receiving a semispherical protuberance, and in this respect for example, the central opening of each belleville washer further includes a curvate volume 336a, 336b for receiving therein the ball-shaped head 410 of the post 406 of the lower plate 400, the curvate volume being similar in form and function to that of the belleville washer of the second embodiment family.

Figure 13A:
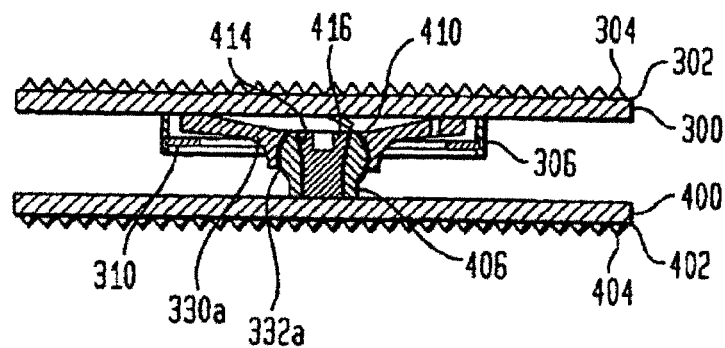
FIGS. 13a-b are side cross-section views of fully assembled embodiments in the third embodiment family, which utilize the corresponding belleville washers illustrated in FIGS. 11a-b mounted between the plates illustrated in FIGS. 12a-b.
Figure 13B:
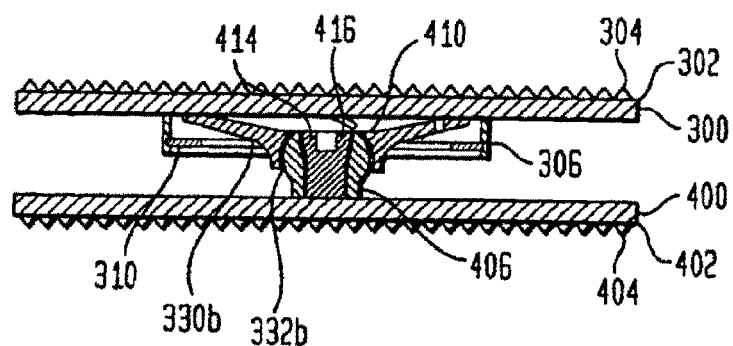

Referring now to FIGS. 13a-b, side cross-sectional views of fully assembled embodiments of the third embodiment family are provided. Each structure includes a belleville washer (selected from those illustrated in FIGS. 11a-b) having its wide end held against the plate 300 of FIG. 10a by the retaining ring 310 and retaining wall 306, and its central opening 332a, 332b rotatably and angulatably secured to the ball-shaped head 410 of the plate 400 of FIG. 10b and 12b by a set screw 416 received in the threaded bore 414 of the head 410 (after the head 410 is placed in the central opening 332a, 332b), similar in this respect to the assembly of the second embodiment family.

Figure 14A:
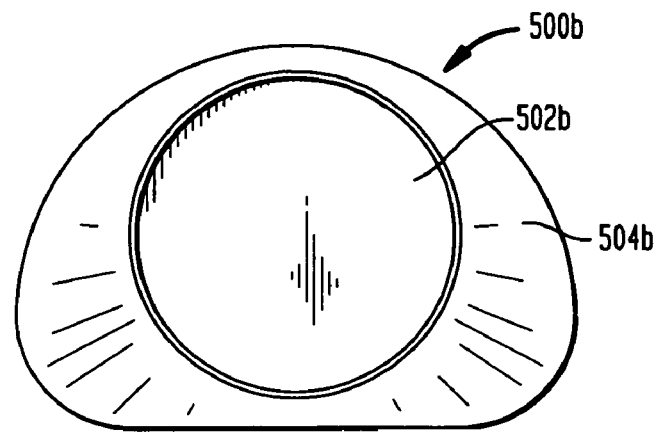
FIGS. 14a-c are bottom plan, side cross-section, and top plan views of a lower plate of a fourth embodiment family of the invention, having a circular recess and rivet holes.
Figure 14B:
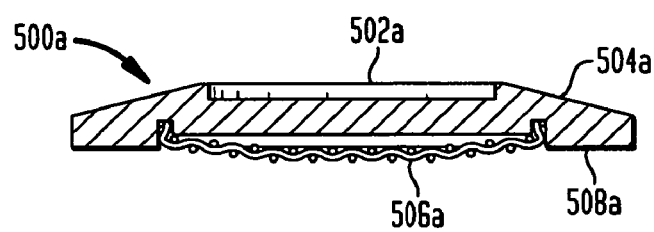
Figure 14C:
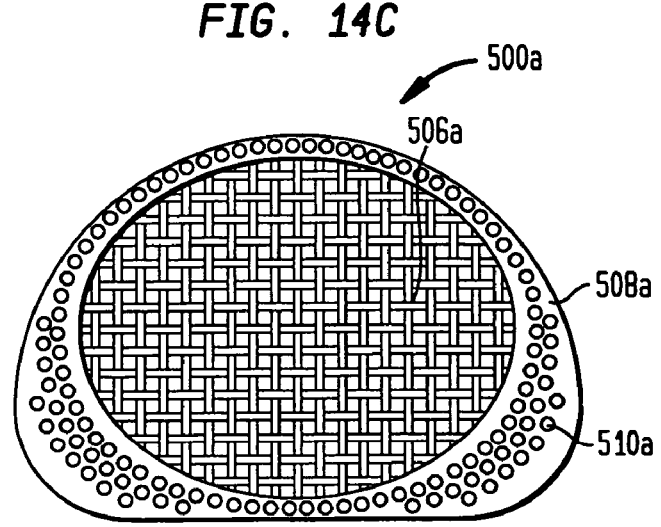
Figure 15A:
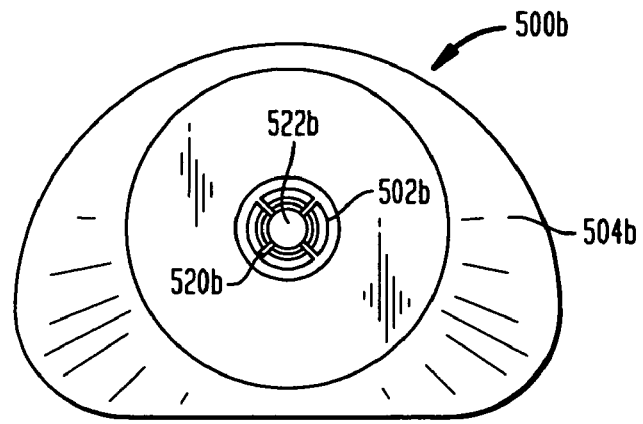
FIGS. 15a-c are bottom plan, side cross-section, and top plan views of an upper plate of the fourth embodiment family, having a semispherical protuberance.
Figure 15B:
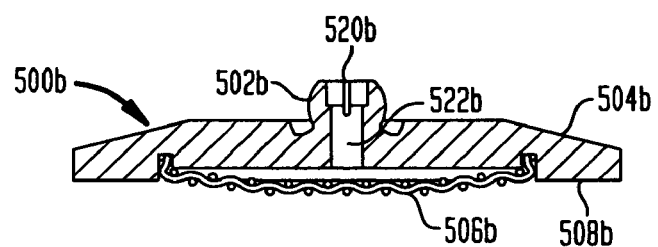
Figure 15C:
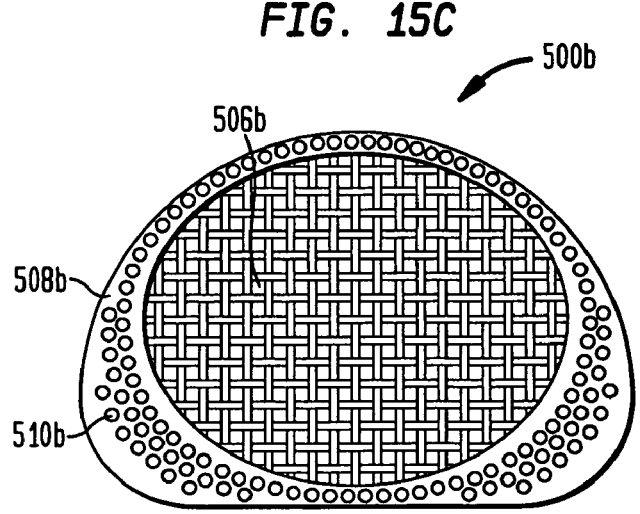

With regard to the fourth embodiment family, and referring now to FIGS. 14a-c and 15a-c, two alternate plates of the invention for use in an artificial disc of the invention are shown in bottom plan views (FIGS. 14a and 15a), side cutaway views (where cross-sectional areas and surfaces viewable behind them are shown) (FIGS. 14b and 15b), and top plan views (FIGS. 14c and 15c). More specifically, FIGS. 14a-b show a bottom plan view and a side cutaway view, respectively, of an alternate lower plate 500a. FIGS. 15a-b show a bottom plan view and a side cutaway view, respectively, of an alternate upper plate 500b.

Figure 17:
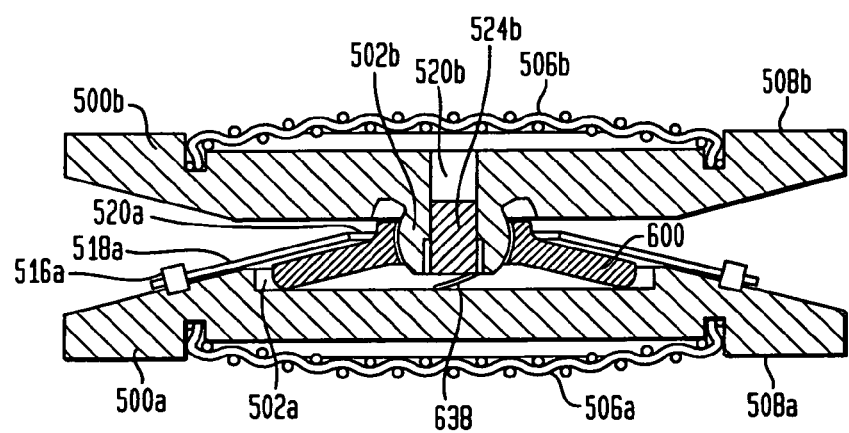
FIG. 17 is a side cross-section view of an assembled embodiment in the fourth embodiment family, which utilizes a spirally slotted belleville washer having a curvate socket mounted between the plate of FIGS. 14a-c and the plate of FIGS. 15a-c.

Each plate 500a-b has an exterior surface 508a-b. Because the artificial disc of the invention is to be positioned between the facing surfaces of adjacent vertebral bodies, the two plates used in the artificial disc are disposed such that the exterior surfaces face away from one another (as best seen in FIG. 17, discussed below). The two plates are to mate with the vertebral bodies so as to not rotate relative thereto, but rather to permit the spinal segments to axially compress and bend relative to one another in manners that mimic the natural motion of the spinal segment. This motion is permitted by the performance of a belleville washer (as described herein) disposed between the secured plates. The mating of the plates to the vertebral bodies and the application of the belleville washer to the plates are described below.

More particularly, each plate 500a-b is a flat plate (preferably made of a metal such as, for example, titanium) having an overall shape that conforms to the overall shape of the respective endplate of the vertebral body with which it is to mate. Further, each plate 500a-b comprises a vertebral body contact element (e.g., a convex mesh 506a-b) (preferably oval in shape) that is attached to the exterior surface (outer surface, or external face) 508a-b of the plate 500a-b to provide a vertebral body contact surface. The mesh 506a-b is secured at its perimeter, by laser welds, to the exterior surface 508a-b of the plate 500a-b. The mesh is domed in its initial undeflected conformation, but deflects as necessary during insertion of the artificial disc between vertebral bodies, and, once the artificial disc is seated between the vertebral bodies, deforms as necessary under anatomical loads to reshape itself to the concave surface of the vertebral endplate. This affords the plate having the mesh substantially superior gripping and holding strength upon initial implantation as compared with other artificial disc products. The mesh further provides an osteoconductive surface through which the bone may ultimately grow. The mesh is preferably comprised of titanium, but can also be formed from other metals and/or non-metals without departing from the scope of the invention.

Each plate 500a-b further comprises at least a lateral ring 510a-b that is osteoconductive, which may be, for example, a sprayed deposition layer, or an adhesive applied beaded metal layer, or another suitable porous coating. This porous ring permits the long-term ingrowth of vertebral bone into the plate, thus permanently securing the prosthesis within the intervertebral space. It shall be understood that this porous layer 510a-b may extend beneath the domed mesh 506a-b as well, but is more importantly applied to the lateral rim of the exterior surface 508a-b of the plate 500a-b that seats directly against the vertebral body.

It should be understood that the convex mesh attachment devices and methods described herein can be used not only with the artificial discs and artificial disc plates described or referred to herein, but also with other artificial discs and artificial disc plates, including, but not limited to, those currently known in the art. Therefore, the description of the mesh attachment devices and methods being used with the artificial discs and artificial disc plates described or referred to herein should not be construed as limiting the application and/or usefulness of the mesh attachment device.

With regard to the disposition of a belleville washer between these two plates, each of the plates 500a-b comprises features for applying the belleville washer thereto, and the various application methods are described below. More specifically, the lower plate 500a includes an inwardly facing surface (inner surface, or internal face) 504a that includes a circular recess 502a for rotationally housing a wide end of a belleville washer and allowing the wide end to expand in unrestricted fashion when the belleville washer is compressed, and the inwardly facing surface 504a also accepts fasteners (e.g., screws, plugs, dowels, or rivets; rivets 516a are used herein as examples) (shown in FIG. 17) for securing a retaining element (e.g., a shield 518a) (the purpose and application of the shield are described below and shown on FIG. 17).

The upper plate 500b includes an inwardly facing surface 504b that includes an inwardly directed semispherical (e.g., ball-shaped) protuberance 502b. The ball-shaped protuberance 502b includes a series of slots 520b that render the ball-shaped protuberance 502b radially compressible and expandable in correspondence with a radial pressure (or a radial component of a pressure applied thereto). The ball-shaped protuberance 502b further includes an axial bore 522b that accepts a deflection preventing element (e.g., a rivet, plug, dowel, or set screw; a rivet 524b is used herein as an example) (shown in FIG. 17). (If a screw is used, the bore can be threaded to accept it.) Prior to the insertion of the rivet 524b, the ball-shaped protuberance 502b can deflect radially inward because the slots 520b will narrow under a radial pressure. The insertion of the rivet 524b eliminates the capacity for this deflection. Therefore, the ball-shaped protuberance 502b, before receiving the rivet 524b, can be compressed to seat in a curvate socket portion of a belleville washer and, once the ball-shaped protuberance 502b has been seated in the curvate socket, the rivet 524b can be inserted into the axial bore 522b to ensure that the ball-shaped protuberance 502b remains held in the curvate socket. A hole can be provided in the opposing plate so that the interior of the device may be readily accessed if a need should arise. It should be understood that the specific dimensions of the ball-shaped protuberance, the mechanism for radial compressibility of the ball-shaped protuberance, and the mechanism for preventing radial compression of the ball-shaped protuberance are not limited to those shown, but rather can be varied and changed without departing from the scope of the invention.

Figure 16A:
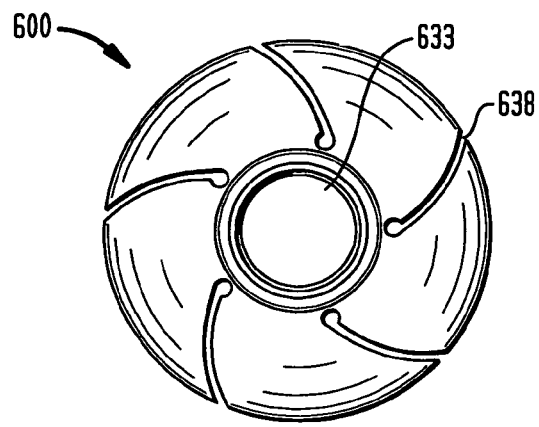
FIGS. 16a-b are top plan and top perspective views of a spirally slotted belleville washer, for use in the fourth embodiment family.
Figure 16B:
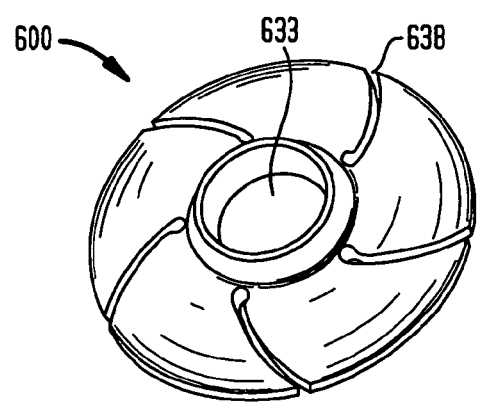

Referring now to FIGS. 16a-b, a belleville washer for use in the fourth embodiment family as an example, is shown in top plan and top perspective views, respectively. More particularly, the belleville washer 600 has a curvate socket 633 (e.g., of a type described above with regard to the other belleville washers described herein), and spiral slots 638. The belleville washer 600 performs in expansion and restoration similarly to the other belleville washers described herein, with regard to their spirally slotted aspects.

Referring now to FIG. 17, a side cross-sectional view of a fully assembled embodiment of the fourth embodiment family is provided. The structure includes a spirally slotted belleville washer 600 of FIGS. 16a-b (although other belleville washers, including any of those described herein, can be used in similar fashion), with its wide end held against the plate 500a of FIGS. 14a-c by a retaining element (e.g., a shield 518a) encompassing the extent of the belleville washer 600. More specifically, the wide end of the belleville washer fits within the circular recess 502a with room to expand when the belleville washer is under compression. Because the diameter of the circular recess is greater than the diameter of the wide end of the belleville washer, unrestrained rotation of the belleville washer relative to the plate is enabled, and compressive loading of the artificial disc (and therefore the belleville washer) results in an unrestrained radial deflection of the belleville washer, both as necessary for proper anatomical response. To prevent removal of the wide end of the belleville washer from the circular recess when the artificial disc is loaded in tension, the shield 518a is placed over the belleville washer and secured by fasteners (e.g., rivets 516a). The shield 518a is preferably frusto-conical such that it has a central hole 520a through which the curvate socket of the belleville washer and the ball-shaped protuberance of the opposing plate can pass to accommodate efficient assembly of the artificial disc. The shield 518a can alternatively or additionally be formed from multiple shield parts. With regard to the narrow end of the belleville washer (the end having the curvate socket), this end is rotatably and angulatably coupled to the ball-shaped protuberance on the opposing plate, as described above.

In embodiments having a ball-and-socket joint as described herein, because the ball-shaped protuberance is held within the curvate socket by a rivet or set screw in the axial bore preventing radial compression of the ball-shaped protuberance, the artificial disc can withstand tension loading of the plates, as necessary for proper anatomical response. More particularly, when a tension load is applied to the plates, the ball-shaped protuberance in the curvate socket seeks to radially compress to fit through the opening of the curvate socket. However, the rivet or set screw in the axial bore of the ball-shaped protuberance prevents the radial compression, thereby preventing the ball-shaped protuberance from exiting the curvate socket. Further, as the wide end of the belleville washer seeks to separate from the plate when there is a tension load, the retaining ring (or the shield) prevents the separation when the belleville washer presses against the inner surface of the ring or shield. Therefore, the assembly does not come apart under normally experienced tension loads. This ensures that no individual parts of the assembly will pop out or slip out from between the vertebral bodies when the patient stretches or hangs while exercising or performing other activities. Thus, in combination with the securing of the plates to the adjacent vertebral bones via the mesh domes, the disc assembly has an integrity similar to the tension-bearing integrity of a healthy natural intervertebral disc.

Further, because the plates in some embodiments are made angulatable relative to one another by the ball-shaped protuberance being rotatably and angulatably coupled in a curvate socket, the disc assembly provides a centroid of motion within the ball-shaped protuberance. Accordingly, in those embodiments, the centroid of motion of the disc assembly remains centrally located between the vertebral bodies, similar to the centroid of motion in a healthy natural intervertebral disc.

Inasmuch as the human body has a tendency to produce fibrous tissues in perceived voids, such as may be found within the interior of the invention, and such fibrous tissues may interfere with the stable and/or predicted functioning of the device, preferred embodiments of the invention will be filled with a highly resilient and biologically inert elastomeric material. Suitable materials may include hydrophilic monomers such as are used in contact lenses. Alternative materials include silicone jellies and collagens such as have been used in cosmetic applications.

While there has been described and illustrated specific embodiments of an artificial disc, it will be apparent to those skilled in the art that variations and modifications are possible without deviating from the broad spirit and principle of the invention. The invention, therefore, shall not be limited to the specific embodiments discussed herein.

What is claimed is:

1. An intervertebral spacer device comprising:
    first and second plates disposed in a spaced apart relationship, each said plate having an inner surface and an outer surface, the inner surfaces of said opposing plates facing one another;
    at least one restoring force providing element disposed between the inner surfaces of said first and second plates, wherein a compressive load applied to the outer surfaces of said first and second plates is counteracted by said at least one restoring force providing element;
    said at least one restoring force providing element including at least one slotted belleville washer having a convex shape when unloaded and a flatter shape when loaded, wherein one or more slots of said belleville washer widen when compressively loaded, wherein said at least one slotted belleville washer is unloaded when no load is applied to said outer surfaces of said first and second plates, and is loaded when said compressive load is applied to said outer surfaces of said first and second plates;
    a retaining wall extending outwardly from the inner surface of the second plate, said retaining wall having an annular recess formed in an inner surface thereof; and
    a retaining ring held in the annular recess of the retaining wall,
    wherein a wide end of said at least one belleville washer is captured by said retaining wall and said retaining ring for maintaining the wide end adjacent the inner surface of said second plate.

2. The intervertebral spacer device of claim 1, wherein at least one of the outer surfaces comprises an osteoconductive feature.

3. The intervertebral spacer device of claim 2, wherein the osteoconductive feature comprises an element that is deformably reshapeable under anatomical loads to securably engage a vertebral body endplate.

4. The intervertebral spacer device of claim 3, wherein the element comprises a wire mesh having a resting shape in the shape of a dome convexly extending from the at least one of said first and second plates.

5. The intervertebral spacer device of claim 1, wherein said at least one belleville washer has at least one spiral slot.

6. The intervertebral spacer device of claim 5, wherein the at least one spiral slot comprises a plurality of spaced apart spiral slots, each of which extends from a locus on a peripheral edge of said at least one belleville washer to a locus that is radially in from the peripheral edge.

7. The intervertebral spacer device of claim 1, wherein said at least one belleville washer has a central opening forming a curvate socket and at least one of said first and second plates has on its inner surface a semispherical protuberance that is rotatably and angulatably couplable to the curvate socket.

8. The intervertebral spacer device of claim 7, wherein the semispherical protrusion comprises a radially deflectable semispherical portion and the curvate socket has an interior volume and an opening leading to the interior volume, the curvate socket accommodating the semispherical portion for free rotation and angulation therein, the semispherical portion fitting through the opening only when radially deflected, the semispherical portion being adapted to receive a deflection preventing element that when applied to the semispherical portion prevents the semispherical portion from fitting through the opening.

9. The intervertebral spacer device of claim 7, wherein the semispherical protuberance is provided by a post structure extending outwardly from one of the inner surfaces, which post structure includes a ball-shaped head.

10. The intervertebral spacer device of claim 9, wherein the post structure further includes a bore that extends axially from the ball-shaped head toward the one of the inner surfaces, and which bore receives therein a deflection preventing element such that prior to an insertion of the deflection preventing element therein, the bore permits the ball-shaped head to compress radially inwardly, and such that after the insertion of the deflection preventing element the ball-shaped head is not readily radially compressible.

11. An artificial intervertebral disc, comprising:
    first and second plates spaced from one another, each said plate including an inwardly facing support surface and an outwardly facing surface;
    at least one slotted belleville washer disposed between the inwardly facing support surfaces such that a compressive load applied to the outwardly facing surfaces is resisted by said at least one belleville washer;
    said at least one belleville washer including a central opening forming a curvate socket;
    said first plate including a semispherical protuberance on the inwardly facing support surface thereof, the semispherical protuberance being rotatably and angulatably couplable to the curvate socket such that said plates are rotatable and angulatable relative to one another thereby; and
    wherein said at least one slotted belleville washer has a convex shape when unloaded, and assumes a flatter shape as the slots widen when compressively loaded;

wherein said at least one slotted belleville washer is unloaded when no load is applied to said outwardly facing surfaces, and is loaded when said compressive load is applied to said outwardly facing surfaces; and a retaining wall extending outwardly from the inwardly facing surface of the second plate, said retaining wall having an annular recess formed in an inner surface thereof; and a retaining ring held in the annular recess of the retaining wall, wherein said retaining wall and retaining ring form an annular groove in which a wide end of said at least one belleville washer is captured such that the wide end is maintained adjacent the inwardly facing surface of said second plate.

12. The artificial intervertebral disc of claim 11, further comprising on at least one of the outwardly facing surfaces a convex wire mesh that is deformably reshapeable under anatomical loads to securably engage a vertebral body endplate.

13. The artificial intervertebral disc of claim 11, wherein the semispherical protrusion comprises a radially deflectable semispherical portion and the curvate socket has an interior volume and an opening leading to the interior volume, the curvate socket accommodating the semispherical portion for free rotation and angulation therein, the semispherical portion fitting through the opening only when radially deflected, the semispherical portion being adapted to receive a deflection preventing element that when applied to the semispherical portion prevents the semispherical portion from fitting through the opening.

14. The artificial intervertebral disc of claim 11, wherein said at least one belleville washer has a plurality of spaced apart spiral slots, each of which extends from a locus on a peripheral edge of said at least one belleville washer to a locus that is radially in from the peripheral edge.

\* \* \* \* \*